(12) United States Patent
Kumagai

(10) Patent No.: US 12,423,996 B2
(45) Date of Patent: Sep. 23, 2025

(54) PASSENGER STATE DETERMINATION DEVICE AND PASSENGER STATE DETERMINATION METHOD

(71) Applicant: Mitsubishi Electric Corporation, Tokyo (JP)

(72) Inventor: Taro Kumagai, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 242 days.

(21) Appl. No.: 18/039,084

(22) PCT Filed: Feb. 12, 2021

(86) PCT No.: PCT/JP2021/005196
§ 371 (c)(1),
(2) Date: May 26, 2023

(87) PCT Pub. No.: WO2022/172391
PCT Pub. Date: Aug. 18, 2022

(65) Prior Publication Data
US 2024/0104942 A1 Mar. 28, 2024

(51) Int. Cl.
*G06V 20/59* (2022.01)
*A61B 5/00* (2006.01)
(Continued)

(52) U.S. Cl.
CPC ............. *G06V 20/59* (2022.01); *B60N 2/002* (2013.01); *G01D 21/00* (2013.01)

(58) Field of Classification Search
CPC ........ G06V 20/59; B60N 2/002; G01D 21/00; A61B 5/00; A61B 5/0245; A61B 5/18;
(Continued)

(56) References Cited

U.S. PATENT DOCUMENTS 10,023,199 B2 * 7/2018 Boos ..................... A61B 5/1103
10,726,576 B2 * 7/2020 Noble ......................... G06T 7/74
2018/0197030 A1 * 7/2018 Yamataka ................ G08G 1/16

FOREIGN PATENT DOCUMENTS

JP 2019-33911 A 3/2019

OTHER PUBLICATIONS

German Office Action for the German Application No. 11 2021 006 203.4, dated Apr. 30, 2024, with a partial translation.

* cited by examiner

*Primary Examiner* — Brandi N Hopkins
(74) *Attorney, Agent, or Firm* — Birch, Stewart, Kolasch & Birch, LLP

(57) ABSTRACT

A passenger state determination device includes: a third determination part finally determining a state of a passenger based on a first determination result as a determination result of the state of the passenger by the first determination part and a second determination result as a determination result of the state of the passenger by the second determination part. The third determination part determines the first determination result to be a final determination result of the state of the passenger in a normal state, and when the first determination result is changed and the third determination part determines that the first determination result after the change is not appropriate, the third determination part determines the second determination result or the first determination result before the change to be a final determination result of the state of the passenger.

10 Claims, 15 Drawing Sheets

(51) Int. Cl.
 *A61B 5/11* (2006.01)
 *A61B 5/18* (2006.01)
 *B60N 2/00* (2006.01)
 *G01D 21/00* (2006.01)

(58) Field of Classification Search
 CPC ........ G08B 21/06; G08B 25/04; G08B 25/10; G08G 1/16; B60W 40/08; B60W 50/14
 See application file for complete search history.

F I G. 4
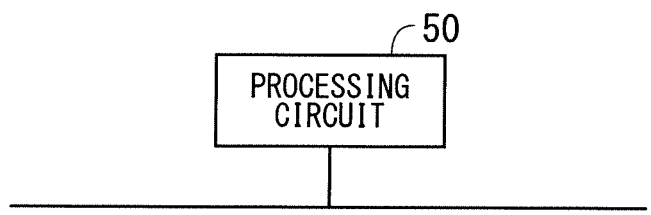

F I G. 8
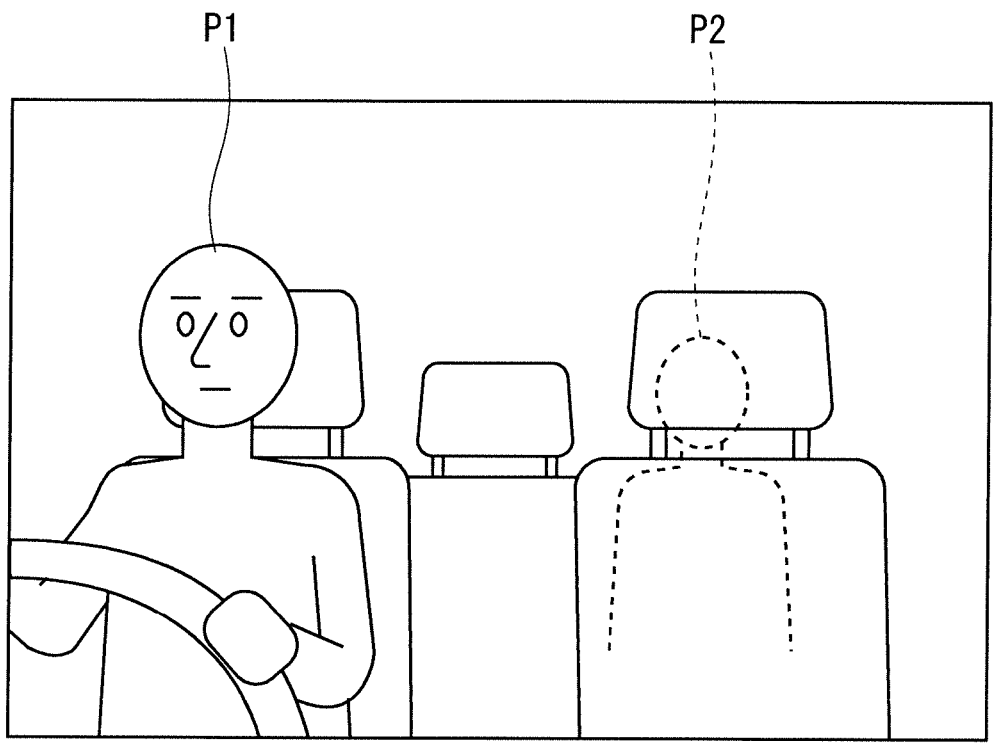

F I G. 1 3
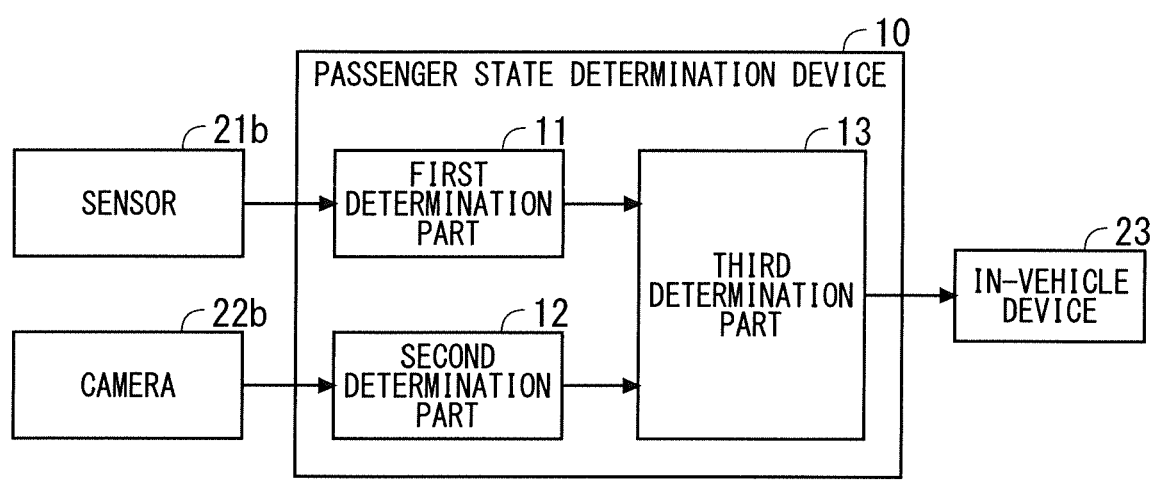

F I G. 14
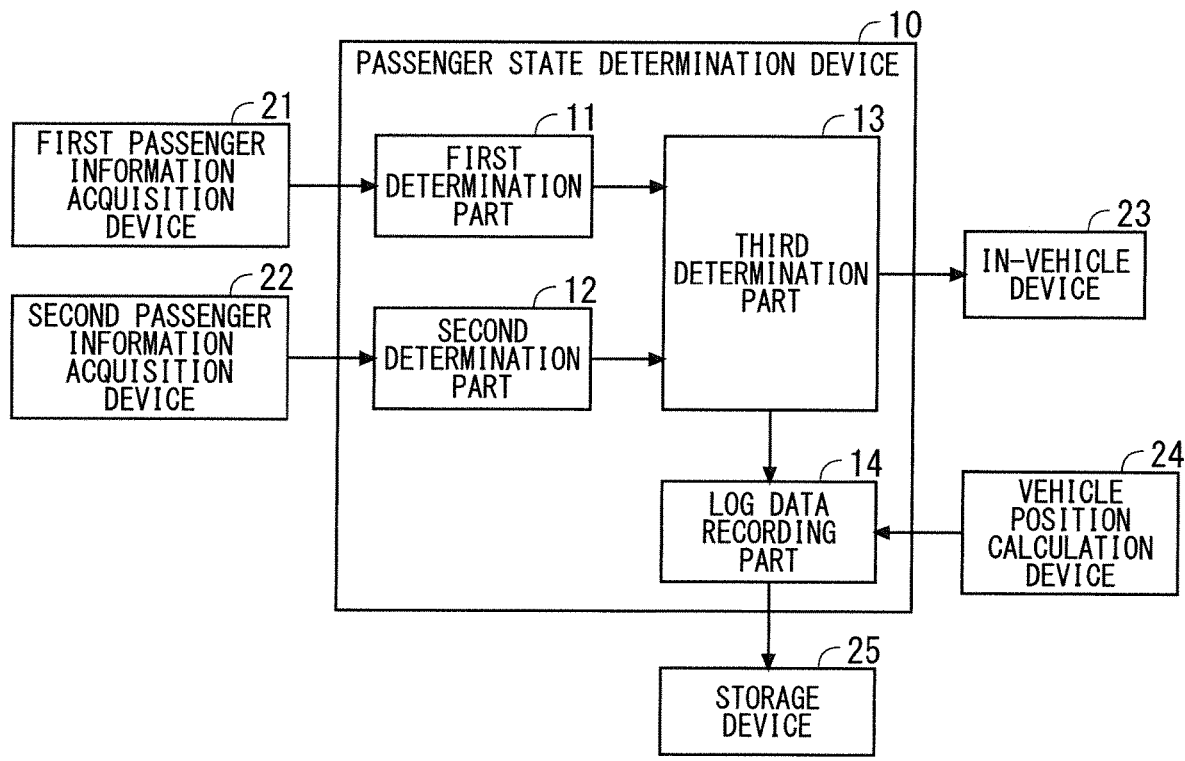

PASSENGER STATE DETERMINATION DEVICE AND PASSENGER STATE DETERMINATION METHOD

TECHNICAL FIELD

The present disclosure relates to a passenger state determination device determining a state of a passenger of a vehicle.

BACKGROUND ART

Promoted is practical use of a passenger state determination device determining a state of a passenger of a vehicle based on information obtained by a camera or a sensor mounted to a vehicle. For example, Patent Document 1 described hereinafter discloses an abnormality detection device detecting abnormality of a passenger by determining a state of the passenger using two types of method. In the abnormality detection device in Patent Document 1, when two determination results each obtained using a method different from each other are different from each other, performed is one of (a) even in a case where one of the two determination results is "not abnormal", when the other one thereof is "abnormal", a final determination is "abnormal", and (b) even in a case where one of the two determination results is "abnormal", when the other one thereof is "not abnormal", a final determination is "not abnormal".

PRIOR ART DOCUMENTS

Patent Document(s)

Patent Document 1: Japanese Patent Application Laid-Open No. 2019-033911

SUMMARY

Problem to be Solved by the Invention

Considered is a case where the abnormality detection device in Patent Document 1 detects a state of a passenger on a front seat (driver seat and front passenger seat) of a vehicle using a camera and a sensor (radio-frequency sensor or ultrasonic sensor, for example). For example, in a case where a driver (passenger on a driver seat) loses consciousness and falls forward, when the other passenger recognizing the driver's state moves his/her face close to the driver seat, the camera erroneously recognizes the face of the other passenger as a face of the driver, and the determination is erroneously "not abnormal". In the meanwhile, the sensor can correctly detect a posture of the driver even when the face of the other passenger gets close to the driver seat, thus the sensor correctly determines the state of the driver to be "abnormal". Thus, processing of finally determining the state of the driver to be "abnormal" when the sensor determines the state thereof to be "abnormal" even in a case where the camera determines the state thereof to be "not abnormal", that is to say, the processing of (a) described above needs to be performed to correctly determine the state of the driver in this case.

For example, when a passenger on the front passenger seat opens up a newspaper and an image of the passenger on the front passenger seat cannot be taken with the camera, the camera erroneously determines a state of the passenger on the front passenger seat to be "abnormal" even when the passenger is not in an abnormal state. In the meanwhile, the sensor can correctly detect a posture of the passenger on the front passenger seat even when the passenger is covered by the newspaper, thus the sensor correctly determines the state of the driver to be "not abnormal". Thus, processing of finally determining the state of the passenger on the front passenger seat to be "not abnormal" when the sensor determines the state thereof to be "not abnormal" even in a case where the camera determines the state thereof to be "abnormal", that is to say, the processing of (b) described above needs to be performed to correctly determine the state of the passenger on the front passenger seat in this case.

In this manner, there are a case of being erroneously determined to be "not abnormal" and a case of being erroneously determined to be "abnormal", thus the processing of (a) and the processing of (b) described above should be applied differently in accordance with contents of the erroneous determination. However, the abnormality detection device of Patent Document 1 performs one of the (a) and (b) described above, thus it is difficult for the technique of Patent Document 1 to prevent erroneous determination in both the two cases described above.

The present disclosure is to solve the above problems, and an object of the present disclosure is to provide a passenger state determination device capable of more reliably preventing erroneous determination of a state of a passenger of a vehicle.

Means to Solve the Problem

A passenger state determination device according to the present disclosure includes: a first determination part determining a state of a passenger of a vehicle by a first method; a second determination part determining a state of the passenger by a second method different from the first method; and a third determination part finally determining a state of the passenger based on a first determination result as a determination result of the state of the passenger by the first determination part and a second determination result as a determination result of the state of the passenger by the second determination part, wherein the third determination part determines the first determination result to be a final determination result of the state of the passenger in a normal state, and when the first determination result is changed, the third determination part determines whether or not the first determination result after the change is appropriate based on the second determination result, and when the third determination part determines that the first determination result after the change is not appropriate, the third determination part determines the second determination result or the first determination result before the change to be a final determination result of the state of the passenger.

Effects of the Invention

According to the present disclosure, erroneous determination of the state of the passenger of the vehicle can be prevented more reliably.

These and other objects, features, aspects and advantages of the present disclosure will become more apparent from the following detailed description when taken in conjunction with the accompanying drawings.

BRIEF DESCRIPTION OF DRAWINGS

FIG. 4 A drawing illustrating an example of a hardware configuration of the passenger state determination device.

FIG. 8 A drawing for explaining an example of an operation of the passenger state determination device according to the embodiment 2.

FIG. 13 A drawing illustrating a configuration of a passenger state determination system according to an embodiment 3.

FIG. 14 A drawing illustrating a configuration of a passenger state determination system according to an embodiment 4.

DESCRIPTION OF EMBODIMENT(S)

Embodiment 1

Figure 1:
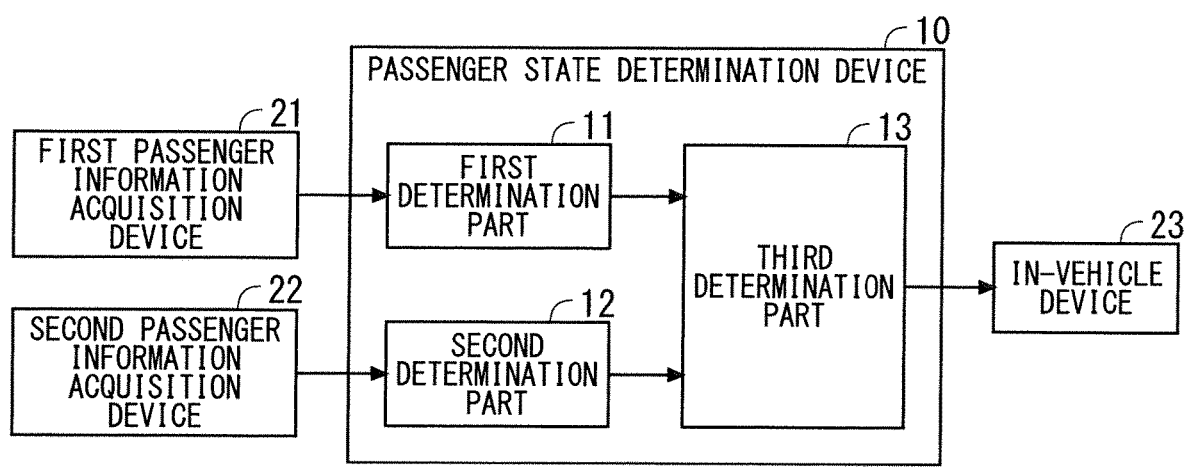
FIG. 1 A drawing illustrating a configuration of a passenger state determination system according to an embodiment 1.

FIG. 1 is a drawing illustrating a configuration of a passenger state determination system according to an embodiment 1. As illustrated in FIG. 1, the passenger state determination system according to the embodiment 1 includes a passenger state determination device 10, and further includes a first passenger information acquisition device 21, a second passenger information acquisition device 22, and an in-vehicle device 23 connected to the passenger state determination device 10.

In the present embodiment, the passenger state determination system is mounted to a vehicle. However, the passenger state determination device 10 needs not necessarily be always disposed in the vehicle, but may also be realized in a mobile device, such as a mobile phone, a smartphone, or a portable navigation device (PND), for example, which can be brought into the vehicle. A part of a function of the passenger state determination device 10 may also be realized in a server which is disposed outside the vehicle and can communicate with the passenger state determination device 10.

Each of the first passenger information acquisition device 21 and the second passenger information acquisition device 22 acquires information of the passenger of the vehicle by a method different from each other. For example, one of the first passenger information acquisition device 21 and the second passenger information acquisition device 22 can be made up of a camera taking an image of the passenger, and the other one thereof can be made up of a sensor (radio-frequency sensor or ultrasonic sensor, for example) acquiring information of a position, a size, and a posture of the passenger. There is no limitation on a type of the sensor, thus also applicable is a voice sensor acquiring voice generated by the passenger or a biological sensor acquiring biological information (a body temperature, a pulse rate, a blood pressure, a respiratory rate, a blood glucose level, and a brain wave, for example) of the passenger, for example.

The passenger state determination device 10 determines the state of the passenger based on the information of the passenger acquired by the first passenger information acquisition device 21 and the second passenger information acquisition device 22. The state of the passenger determined by the passenger state determination device 10 is not limited to a physical condition (presence or absence of abnormality and presence or absence of sleepiness, for example), however, any state such as a body type, age, or sex, for example, is also applicable.

The in-vehicle device 23 is an optional apparatus, an operation of which is controlled in accordance with the state of the passenger determined by the passenger state determination device 10. Considered as the in-vehicle device 23 is, for example, an automatic driving device evacuating the vehicle to a safe place when abnormality occurs in a physical condition of the driver, a warning device emitting warning when the driver feels sleepy, an air-bag device controlling expansion of an air-bag of each seat in accordance with a body type of the passenger, and an individual authentication device performing an individual authentication of the passenger in consideration of age and sex of the passenger.

As illustrated in FIG. 1, the passenger state determination device 10 includes a first determination part 11, a second determination part 12, and a third determination part 13. The first determination part 11 determines the state of the passenger of the vehicle based on the information of the passenger acquired by the first passenger information acquisition device 21. The second determination part 12 determines the state of the passenger based on the information of the passenger acquired by the second passenger information acquisition device 22. That is to say, the first determination part 11 determines the state of the passenger by a first method, and the second determination part 12 determines the state of the passenger by a second method different from the first method. Hereinafter, a determination result of the state of the passenger by the first determination part 11 (by the first method) is referred to as "the first determination result", and a determination result of the state of the passenger by the second determination part 12 (by the second method) is referred to as "the second determination result".

The third determination part 13 finally determines the state of the passenger based on the first determination result and the second determination result, and outputs the final determination result to the in-vehicle device 23. Specifically, the third determination part 13 determines the first determination result to be the final determination result in a normal state. However, when the first determination result is changed, the third determination part 13 determines whether or not the first determination result after the change is appropriate based on the second determination result, and when the third determination part 13 determines that the first determination result after the change is not appropriate, the third determination part 13 determines the second determination result to be the final determination result of the state of the passenger. More specifically, in the case where the first determination result is changed, the third determination part 13 determines that the first determination result after the change is appropriate when the first determination result after the change and the second determination result are the same as each other. However, the third determination part 13 determines that the first determination result after the change is not appropriate when the first determination result after the change and the second determination result are not the same as each other.

In this manner, when the first determination result is changed, the third determination part 13 determines whether or not the first determination result after the change is appropriate, thereby determining whether or not the change of the first determination result is caused by erroneous determination. When it is determined that the first determination result after the change is not appropriate, that is to say, when it is determined that the change of the first determination result after the change is caused by the erroneous determination, the third determination part 13 adopts the second determination result to be the final determination result, thereby preventing the first determination result which is erroneously determined from being output as the final determination result. This method is effective both in a case where the erroneous determination of "abnormal" occurs and in a case where the erroneous determination of "not abnormal" occurs in the first determination result, thus the erroneous determination of the state of the passenger of the vehicle can be prevented more reliably.

Figure 2:
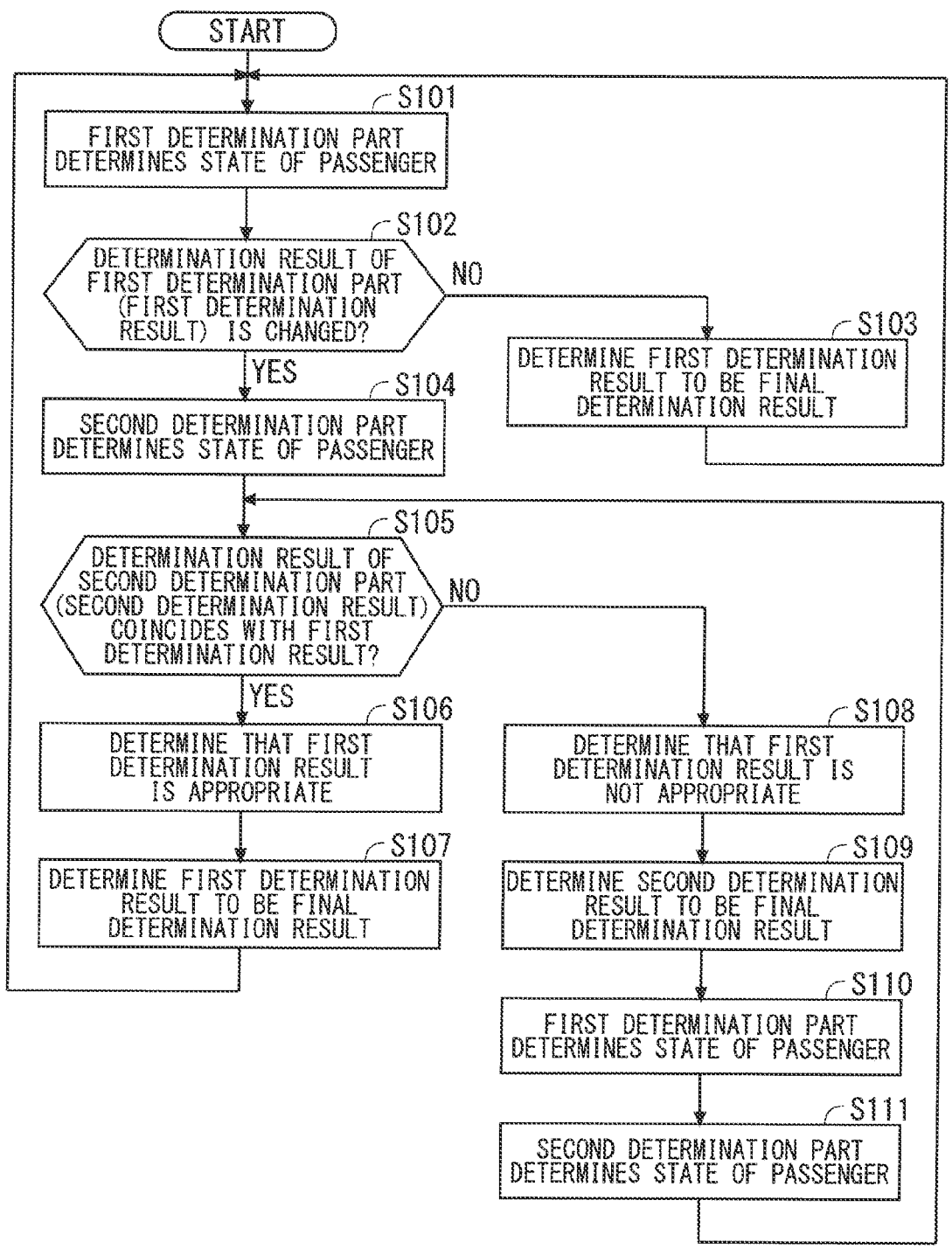
FIG. 2 A flow chart illustrating an operation of a passenger state determination device according to the embodiment 1.

FIG. 2 is a flow chart illustrating an operation of the passenger state determination device 10 according to the embodiment 1. The operation of the passenger state determination device 10 is described hereinafter with reference to this flow chart. In the description herein, one passenger is in the vehicle for simplifying the description. Processing in FIG. 2 is performed on each passenger when the plurality of passengers are in the vehicle.

When the passenger state determination device 10 is activated, the first determination part 11 firstly determines the state of the passenger based on the information of the passenger acquired by the first passenger information acquisition device 21 (Step S101). Next, the third determination part 13 confirms whether or not the first determination result as the determination result by the first determination part 11 is the same as the previous first determination result, thereby determines whether or not the first determination result is changed (Step S102).

In Step S102 immediately after activating the passenger state determination device 10, there is no previous first determination result, thus the first determination result may be considered to be changed or not to be changed. That is to say, in Step S102 immediately after the activation, both the determinations of YES and NO are applicable. However, it is preferable that the determination is YES in Step S102 immediately after the activation by reason that appropriateness of the first determination result immediately after the activation can be determined.

When the first determination result is not changed (NO in Step S102), the third determination part 13 outputs the first determination result as the final determination result to the in-vehicle device 23 (Step S103).

When the first determination result is changed (YES in Step S102), the second determination part 12 determines the state of the passenger based on the information of the passenger acquired by the second passenger information acquisition device 22 (Step S104). Then, the third determination part 13 compares the first determination result and the second determination result (Step S105). When the first determination result and the second determination result are the same as each other (YES in Step S105), the third determination part 13 determines that the first determination result is appropriate (Step S106). In this case, the third determination part 13 outputs the first determination result as the final determination result to the in-vehicle device 23 (Step S107), and the processing returns to Step S101.

Steps S103 and S107 are performed when the erroneous determination does not occur in the first determination result. The "normal state" described above corresponds to a state where Step S103 or S107 is executed.

In the meanwhile, when the first determination result and the second determination result are not the same as each other (NO in Step S105), the third determination part 13 determines that the first determination result is not appropriate (Step S108). In this case, the third determination part 13 outputs the second determination result as the final determination result to the in-vehicle device 23 (Step S109).

After Step S109, the first determination part 11 determines the state of the passenger based on the information of the passenger acquired by the first passenger information acquisition device 21 (Step S110), the second determination part 12 determines the state of the passenger based on the information of the passenger acquired by the second passenger information acquisition device 22 (Step S111), and the processing returns to Step S105 to compare the first determination result acquired in Step S110 and the second determination result acquired in Step S111. The processing in Steps S108 to S111 are repeated until the first determination result acquired in Step S110 and the second determination result acquired in Step S111 are the same as each other (until the determination is to be YES in Step S105), and during the processing, the third determination part 13 continuously outputs the second determination result as the final determination result to the in-vehicle device 23.

When the first determination result acquired in Step S110 and the second determination result acquired in Step S111 are the same as each other (YES in Step S105), the third determination part 13 determines that the first determination result acquired in Step S110 is appropriate (Step S106). In this case, the processing enters the normal state again, the third determination part 13 outputs the first determination result acquired in Step S110 as the final determination result to the in-vehicle device 23 (Step S107), and the processing returns to Step S101.

MODIFICATION EXAMPLE

In the embodiment 1, the third determination part 13 determines the first determination result to be the final determination result in the normal state, and when the first determination result and the second determination result are not the same as each other after the first determination result is changed, the third determination part 13 determines the second determination result to be the final determination result of the state of the passenger. However, when each of the first determination result and the second determination result has two choices such as "not abnormal" and "abnormal" or "adult" and "child", the second determination result which is not the same as the first determination result after the change should be the same as the first determination result before the change. Thus, when the first determination result and the second determination result are not the same as each other after the first determination result is changed, the third determination part 13 may maintain the first determination result before the change as the final determination result of the state of the passenger.

Figure 3:
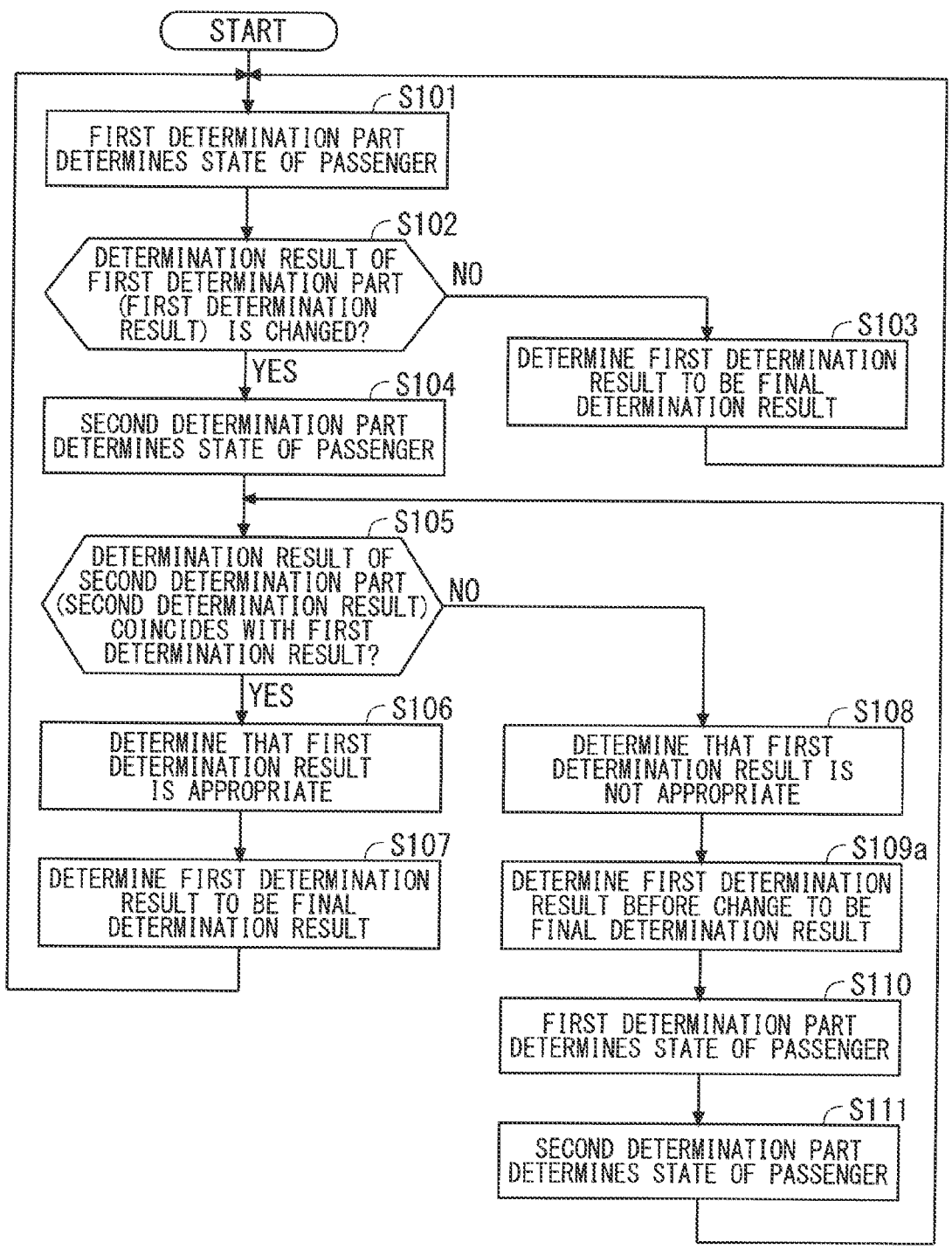
FIG. 3 A flow chart illustrating a modification example of the operation of the passenger state determination device according to the embodiment 1.

FIG. 3 illustrates a flow chart of an operation of the passenger state determination device 10 which is applicable when each of the first determination result and the second determination result has two choices. The flow chart in FIG. 3 is the same as that in FIG. 2 except that Step S109 in FIG. 2 is replaced with Step S109a in which the third determination part 13 determines the first determination result before the change to be the final determination result. The other steps in the flow chart in FIG. 3 is similar to those in FIG. 2, thus the description herein is omitted.

[Example of Hardware Configuration]

Figure 5:
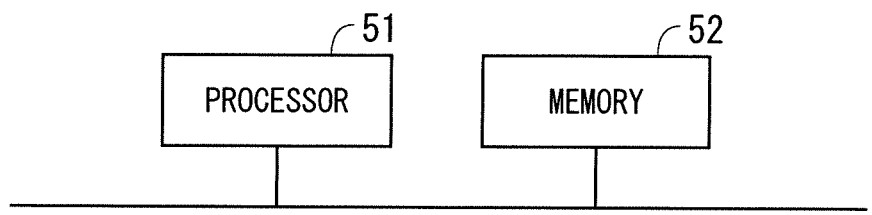
FIG. 5 A drawing illustrating an example of a hardware configuration of the passenger state determination device.

FIG. 4 and FIG. 5 are drawings each illustrating an example of a hardware configuration of the passenger state determination device 10. Each function of constituent elements of the passenger state determination device 10 illustrated in FIG. 1 is achieved by a processing circuit 50 illustrated in FIG. 4, for example. That is to say, the passenger state determination device 10 includes the processing circuit 50 for determining the state of the passenger of the vehicle by the first method, determining the state of the passenger of the vehicle by the second method different from the first method, and finally determining the state of the passenger based on the first determination result as the determination result of the state of the passenger by the first method and the second determination result as the determination result of the state of the passenger by the second method, wherein the processing circuit 50 determines the first determination result to be the final determination result of the state of the passenger in the normal state, and when the first determination result is changed, the processing circuit 50 determines whether or not the first determination result after the change is appropriate based on the second determination result, and when the processing circuit 50 determines that the first determination result after the change is not appropriate, the processing circuit 50 determines the second determination result or the first determination result before the change to be the final determination result of the state of the passenger. The processing circuit 50 may be dedicated hardware, or may also be made up using a processor (also referred to as a central processing unit (CPU), a processing device, an arithmetic device, a microprocessor, a microcomputer, or a digital signal processor (DSP)) for executing a program stored in a memory.

When the processing circuit 50 is the dedicated hardware, a single circuit, a complex circuit, a programmed processor, a parallel-programmed processor, an application specific integrated circuit (ASIC), a field-programmable gate array (FPGA), or a combination of them, for example, falls under the processing circuit 50. Each function of the constituent elements of the passenger state determination device 10 may be achieved by an individual processing circuit, or functions thereof may be collectively achieved by one processing circuit.

FIG. 5 illustrates an example of a hardware configuration of the passenger state determination device 10 in a case where the processing circuit 50 is made up using a processor 51 executing a program. In this case, the functions of the constituent elements of the passenger state determination device 10 are achieved by software etc. (software, firmware, or combination of software and firmware). The software etc. is described as a program and is stored in a memory 52. The processor 51 reads out and executes a program stored in the memory 52, thereby achieving the function of each part. That is to say, the passenger state determination device 10 includes the memory 52 storing programs which consequently execute, when executed by the processor 51: the processing of determining the state of the passenger of the vehicle by the first method; the processing of determining the state of the passenger of the vehicle by the second method different from the first method; and the processing of finally determining the state of the passenger based on the first determination result as the determination result of the state of the passenger by the first method and the second determination result as the determination result of the state of the passenger by the second method, wherein the program determines the first determination result to be the final determination result of the state of the passenger in the normal state, and when the first determination result is changed, the program determines whether or not the first determination result after the change is appropriate based on the second determination result, and when the program determines that the first determination result after the change is not appropriate, the program determines the second determination result or the first determination result before the change to be the final determination result of the state of the passenger. In other words, this program is also deemed to make a computer execute a procedure or a method of the constituent elements of the passenger state determination device 10.

Herein, the memory 52 may be a non-volatile or volatile semiconductor memory such as a RAM (Random Access Memory), a ROM (Read Only Memory), a flash memory, an EPROM (Electrically Programmable Read Only Memory), or an EEPROM (Electrically Erasable Programmable Read Only Memory), an HDD (Hard Disk Drive), a magnetic disc, a flexible disc, an optical disc, a compact disc, a mini disc, a DVD (Digital Versatile Disc), or a drive device of them, or any storage medium which is to be used in the future.

Described above is a configuration that the functions of the constituent elements of the passenger state determination device 10 are achieved by one of the hardware and the software. The configuration is not limited thereto, however, also applicable is a configuration that some constituent element of the passenger state determination device 10 is achieved by dedicated hardware and the other some constituent element thereof is achieved by software, for example. For example, the function of some constituent element can be achieved by the processing circuit 50 as the dedicated hardware, and the function of the other constituent element can be achieved by the processing circuit 50 as the processor 51 reading out and executing the program stored in the memory 52.

As described above, the passenger state determination device 10 can achieve each function described above by the hardware, the software, or the combination of them, for example.

Embodiment 2

Figure 6:
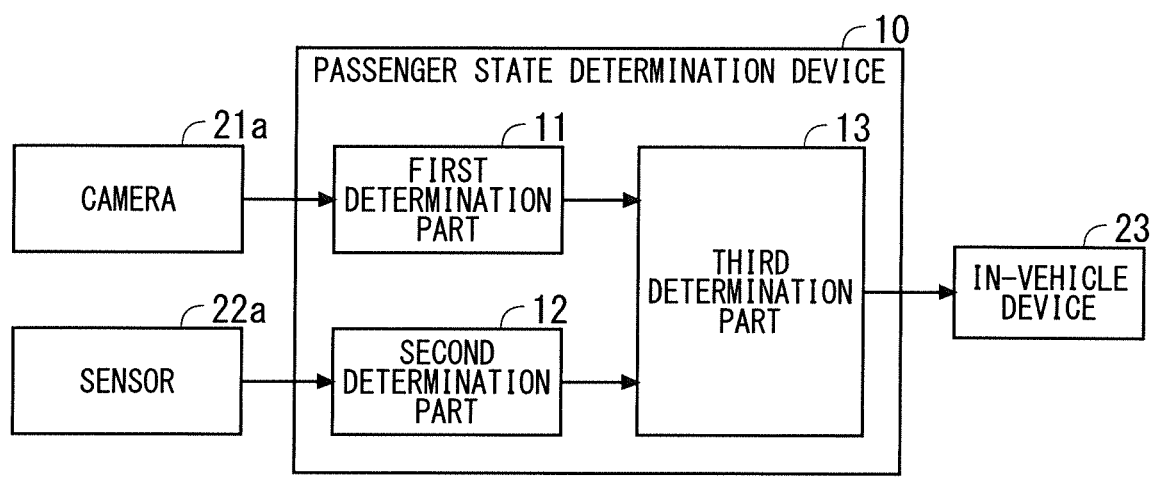
FIG. 6 A drawing illustrating a configuration of a passenger state determination system according to an embodiment 2.

FIG. 6 is a drawing illustrating a configuration of a passenger state determination system according to an embodiment 2. In the passenger state determination system in FIG. 6, a camera 21a taking an image of the passenger of the vehicle is used as the first passenger information acquisition device 21, and a sensor 22a acquiring information such as a position, a size, and a posture of the passenger is used as the second passenger information acquisition device 22. The sensor 22a is a radio-frequency sensor or an ultrasonic sensor. That is to say, in the passenger state determination device 10 of the embodiment 2, the first determination part 11 determines the state of the passenger based on the image of the passenger taken with the camera 21a, and the second determination part 12 determines the state of the passenger based on the information of the passenger detected by the sensor 22a.

Figure 7:
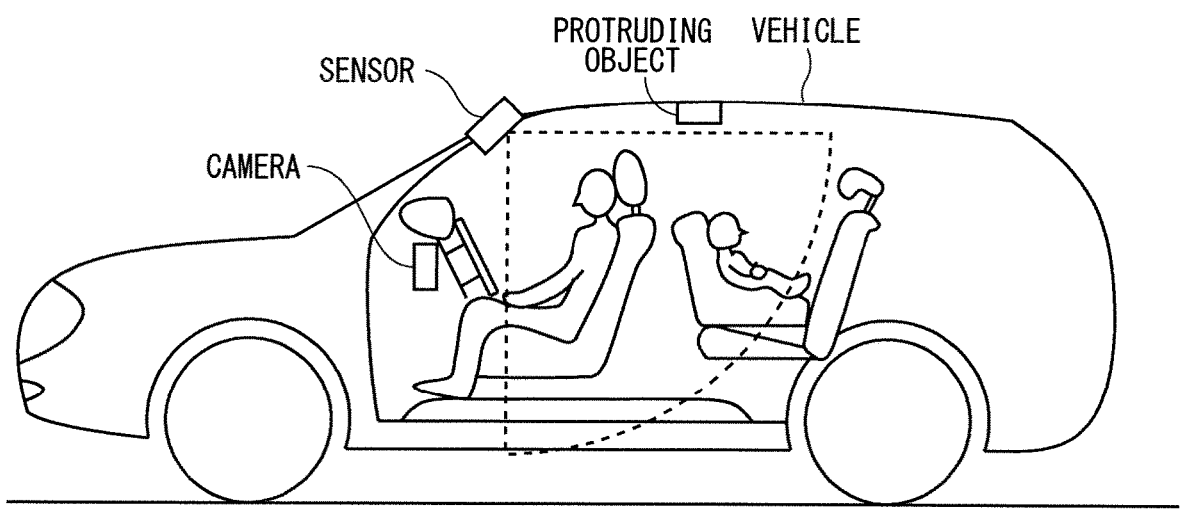
FIG. 7 A drawing illustrating an example of a position where a sensor is disposed.

The sensor 22a as the radio-frequency sensor or the ultrasonic sensor is preferably disposed on an upper portion of a front seat (for example, near an overhead console or an upper portion of a front glass) in a vehicle as illustrated in FIG. 7. A range of radio wave or electromagnetic wave output from the sensor 22a in a traveling direction (range surrounded by a dotted line in FIG. 7) is preferably set to avoid a protruding object (for example, a display device for a rear seat, or a window or an open-close switch of a window of a sunroof). The position of the sensor 22a and the traveling direction of the output radio wave or electromagnetic wave are set in such a manner, thus the sensor 22a can receive reflective wave from a wide range in the vehicle, and a dead angle region of the sensor 22a can be reduced. FIG. 7 illustrates that the traveling direction described above is set to avoid the protruding object in a cross section of the vehicle, however, the traveling direction described above may be set to avoid the protruding object in a flat surface, not shown in the drawings, of a ceiling part of the vehicle.

The operation of the passenger state determination device 10 according to the embodiment 2 is similar to that in the flow chart illustrated in FIG. 2. Thus, the description of the operation of the passenger state determination device 10 using the flow chart is omitted in the present embodiment, and the operation of the passenger state determination device 10 is described by indicating an example of a situation where the passenger state determination device 10 is actually used.

Assumed in the present embodiment is a situation where the passenger state determination device 10 determines presence or absence of abnormality of the passenger on a front seat (a driver seat and a front passenger seat) of the vehicle. The camera 21a is a center console of a vehicle or a wide angle camera disposed near a center cluster to take an image of a region including a driver seat and a front passenger seat.

Assumed as a first example is a state where a passenger P1 (driver) on a driver seat and a passenger P2 on a rear seat sit on the seats in the vehicle. At this time, an image as illustrated in FIG. 8 is take with the camera 21a. The image in FIG. 8 includes the passenger P1 on the driver seat, however, the passenger P2 on the rear seat is located behind a backrest of a front passenger seat.

In the normal state, the third determination part 13 of the passenger state determination device 10 determines the first determination result as the state of the passenger determined by the first determination part 11 to be the final determination result based on the image taken with the camera 21a. Thus, when the first determination part 11 determines that the state of the passenger P1 on the driver seat is "not abnormal" based on the image in FIG. 8, the final determination result of the state of the passenger P1 on the driver seat is determined to be "not abnormal".

Figure 9:
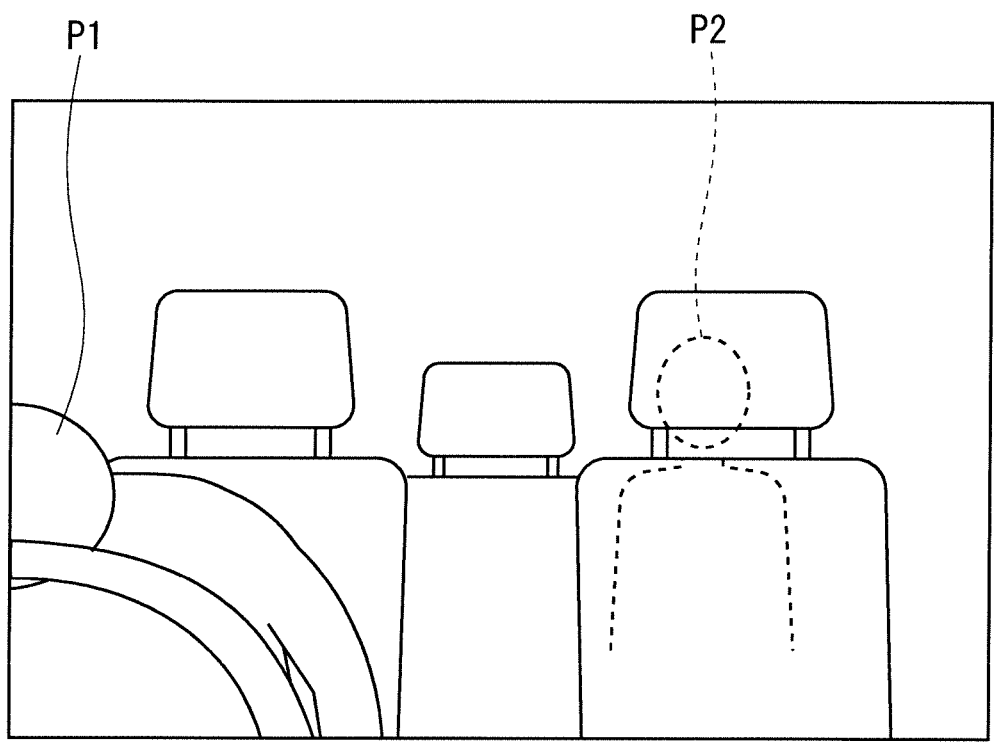
FIG. 9 A drawing for explaining an example of an operation of the passenger state determination device according to the embodiment 2.

Subsequently, it is assumed that the passenger P1 on the driver seat loses consciousness and falls forward, and the camera 21a takes an image as illustrated in FIG. 9. The first determination part 11 determines the state of the passenger P1 on the driver seat to be "abnormal" based on the image in FIG. 9, and changes the first determination result from "not abnormal" to "abnormal". When the first determination result is changed, the second determination part 12 determines the state of the passenger P1 on the driver seat based on the information (a position and a posture of the passenger P1 on the driver seat) acquired by the sensor 22a. When the passenger P1 on the driver seat loses the posture as illustrated in FIG. 9, the second determination part 12 also determines the state of the passenger P1 to be "abnormal". In this manner, when the first determination result and the second determination result are the same as each other, the third determination part 13 determines that the first determination result after the change is appropriate, and determines "abnormal" of the first determination result to be the final determination result of the state of the passenger P1 on the driver seat.

Figure 10:
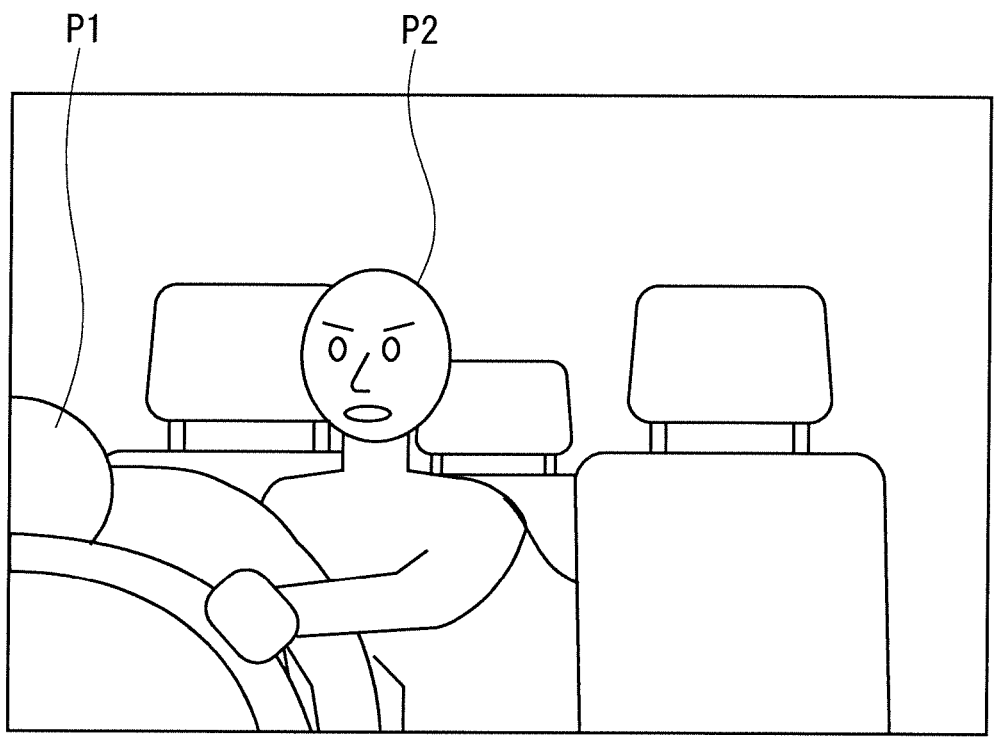
FIG. 10 A drawing for explaining an example of an operation of the passenger state determination device according to the embodiment 2.

For example, it is assumed that the passenger P2 on the rear seat recognizes the abnormality of the passenger P1 on the driver seat, and leans from the rear seat toward the driver seat to perform an operation of a handle of the vehicle, and an image illustrated in FIG. 10 is taken with the camera 21a. At this time, when the first determination part 11 erroneously recognizes a face of the passenger P2 on the rear seat as a face of the passenger P1 on the driver seat, the first determination part 11 erroneously determines the state of the passenger P1 on the driver seat to be "not abnormal", and the first determination result is changed from "abnormal" to "not abnormal". When the first determination result is changed, the second determination part 12 determines the state of the passenger P1 on the driver seat based on the information acquired by the sensor 22a. The sensor 22a can correctly detect the posture of the passenger P1 on the driver seat even when the face of the passenger P2 on the rear seat is located near the driver seat, thus the second determination part 12 correctly determines the state of the passenger P1 on the driver seat to be "abnormal". In this manner, when the first determination result after the change and the second determination result are not the same as each other, the third determination part 13 determines that the first determination result after the change is not appropriate, and determines "abnormal" of the second determination result (or the first determination result before the change) to be the final determination result of the state of the passenger P1 on the driver seat. Thus, the first determination result which is erroneously determined is prevented from being determined to be the final determination result, and the erroneous determination of the state of the passenger P1 on the driver seat is prevented.

When the passenger P1 on the driver seat recovers consciousness and returns to the state as illustrated in FIG. 8, both the first determination part 11 and the second determination part 12 determine the state of the passenger P1 on the driver seat to be "not abnormal", and the first determination result and the second determination result are the same as each other, thus the third determination part 13 enters the normal state again. Thus, the third determination part 13 determines "not abnormal" of the first determination result to be the final determination result of the state of the passenger P1 on the driver seat, and the correct determination is maintained.

When the vehicle is suspended while the passenger P1 on the driver seat does not recover consciousness and the passenger P2 on the rear seat stops the operation of the handle to enter the state as illustrated in FIG. 9, both the first determination part 11 and the second determination part 12 determine the state of the passenger P1 on the driver seat to be "abnormal", and the first determination result and the second determination result are the same as each other, thus the third determination part 13 enters the normal state again. Thus, the third determination part 13 determines "abnormal" of the first determination result to be the final determination result of the state of the passenger P1 on the driver seat, and the correct determination is maintained also in this case.

Assumed as a second example is a state where the passenger P1 (driver) on the driver seat and a passenger P2 on a front passenger seat sit on the seats in the vehicle. At this time, an image as illustrated in FIG. 11 is take with the camera 21a.

In the normal state, the third determination part 13 of the passenger state determination device 10 determines the first determination result as the state of the passenger determined by the first determination part 11 to be the final determination result based on the image taken with the camera 21a. Thus, when the first determination part 11 determines that the state of the passenger P3 on the front passenger seat is "not abnormal" based on the image in FIG. 11, the final determination result of the state of the passenger P3 on the front passenger seat is determined to be "not abnormal".

Figure 12:
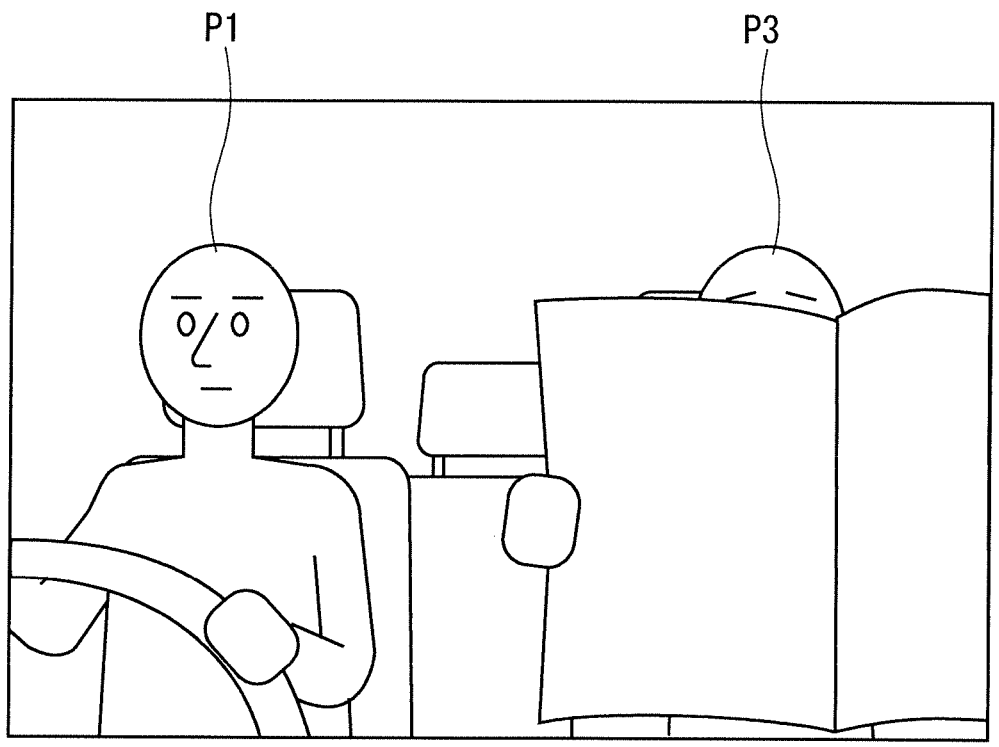
FIG. 12 A drawing for explaining an example of an operation of the passenger state determination device according to the embodiment 2.

Subsequently, it is assumed that passenger P3 on the front passenger seat opens up a newspaper and an image illustrated in FIG. 12 is taken with the camera 21a. The first determination part 11 cannot recognize the passenger P3 on the front passenger seat covered by the newspaper, thus erroneously determines the state of the passenger P3 of the front passenger seat to be "abnormal", and the first determination result is changed from "not abnormal" to "abnormal". When the first determination result is changed, the second determination part 12 determines the state of the passenger P3 on the front passenger seat based on the information acquired by the sensor 22a. The sensor 22a can acquire the information of the passenger P3 of the front passenger seat covered by the newspaper, thus the second determination part 12 correctly determines the state of the passenger P3 on the front passenger seat to be "not abnormal". In this manner, when the first determination result after the change and the second determination result are not the same as each other, the third determination part 13 determines that the first determination result after the change is not appropriate, and determines "abnormal" of the second determination result (or the first determination result before the change) to be the final determination result of the state of the passenger P3 on the front passenger seat. Thus, the first determination result which is erroneously determined is prevented from being determined to be the final determination result, and the erroneous determination of the state of the passenger P3 on the front passenger seat is prevented.

Figure 11:
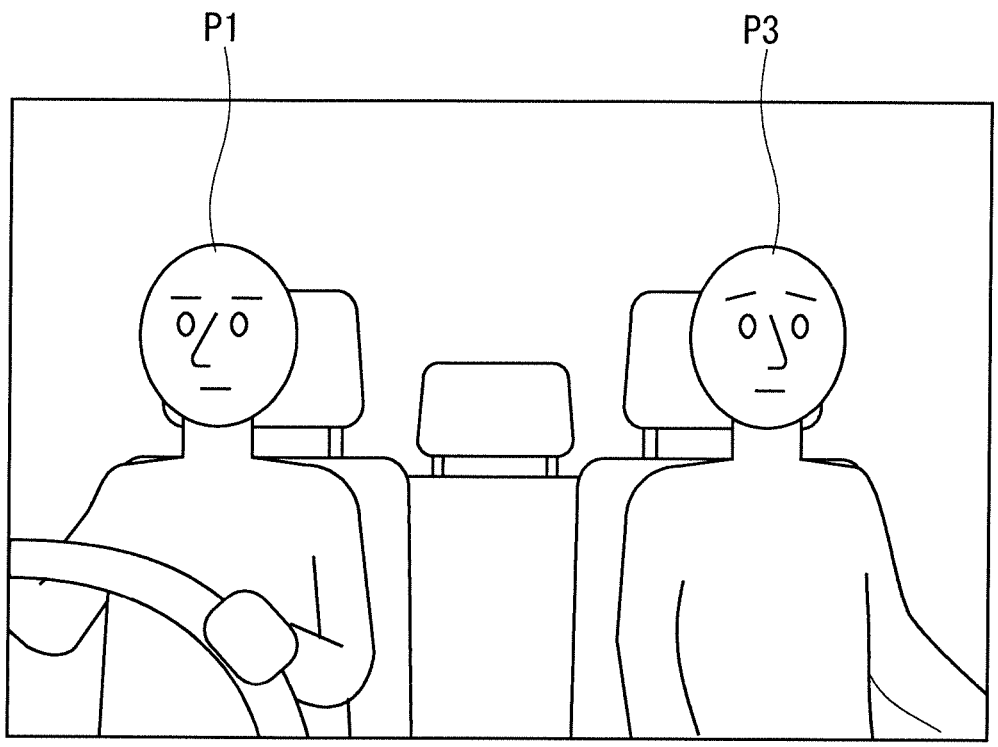
FIG. 11 A drawing for explaining an example of an operation of the passenger state determination device according to the embodiment 2.

When the passenger P3 on the front passenger seat closes the newspaper and returns to the state as illustrated in FIG. 11, both the first determination part 11 and the second determination part 12 determine the state of the passenger P3 on the front passenger seat to be "not abnormal", and the first determination result and the second determination result are the same as each other, thus the third determination part 13 enters the normal state again. Thus, the third determination part 13 determines "not abnormal" of the first determination result to be the final determination result of the state of the passenger P3 on the front passenger seat, and the correct determination is maintained.

When the passenger P3 on the front passenger seat loses consciousness and falls while opening up the newspaper, both the first determination part 11 and the second determination part 12 determine the state of the passenger P3 on the front passenger seat to be "abnormal", and the first determination result and the second determination result are the same as each other, thus the third determination part 13 enters the normal state again. Thus, the third determination part 13 determines "abnormal" of the first determination result to be the final determination result of the state of the passenger P3 on the front passenger seat, and the correct determination is maintained also in this case.

In this manner, the passenger state determination device 10 can prevent the occurrence of the erroneous determination in the final determination result in both the case where the first determination part 11 erroneously determines the state to be "not abnormal" and the case where the first determination part 11 erroneously determines the state to be "abnormal".

Embodiment 3

Described in the embodiment 2 is the example that the first passenger information acquisition device 21 is the camera and the second passenger information acquisition device 22 is the sensor, however, on the contrary, it is also applicable that the first passenger information acquisition device 21 is the sensor and the second passenger information acquisition device 22 is the camera.

Described in the embodiment 3 is an example that a sensor 21b acquiring information such as a position, a size, and a posture of a passenger is used as the first passenger information acquisition device 21, and a camera 21a taking an image of a passenger of the vehicle is used as the second passenger information acquisition device 22. That is to say, in the passenger state determination device 10 of the embodiment 3, the first determination part 11 determines the state of the passenger based on the information of the passenger detected by the sensor 21b, and the second determination part 12 determines the state of the passenger based on the image of the passenger taken with the camera 21a.

The operation of the passenger state determination device 10 according to the embodiment 3 is also similar to that in the flow chart illustrated in FIG. 2. Thus, the description of the operation of the passenger state determination device 10 using the flow chart is omitted also in the present embodiment, and the operation of the passenger state determination device 10 is described by indicating an example of a situation where the passenger state determination device 10 is actually used.

Assumed in the present embodiment is a situation where the passenger state determination device 10 determines a body type of the passenger ("adult" or "child") as the state of the passenger of the vehicle. For example, assumed is a state where a child passenger is located on a child seat disposed on the rear seat of the vehicle.

In the normal state, the third determination part 13 of the passenger state determination device 10 determines the first determination result as the state of the passenger determined by the first determination part 11 to be the final determination result based on the information acquired by the sensor 21b. Thus, when the first determination part 11 determines that a passenger on the child seat is "child", the final determination result of the state of the passenger on the child seat is "child".

Subsequently, it is assumed that the other passenger gets close to the child seat to take care of the child, and as a result, the sensor 21b cannot distinguish the passenger on the child seat from the other passenger, thus erroneously recognizes that the passenger on the child seat and the other passenger as one passenger, for example. In this case, the first determination part 11 erroneously determines the passenger on the child seat to be "adult", and the first determination result is changed from "child" to "adult". When the first determination result is changed, the second determination part 12 determines the state of the passenger on the child seat based on the image taken with the camera 22b. Recognized from the image taken with the camera 22b is the other passenger near the child seat, thus the second determination part 12 correctly determines that the passenger on the child seat to be "child". In this manner, when the first determination result after the change and the second determination result are not the same as each other, the third determination part 13 determines that the first determination result after the change is not appropriate, and determines "child" of the second determination result (or the first determination result before the change) to be the final determination result of the state of the passenger on the child seat. Thus, the first determination result which is erroneously determined is prevented from being determined to be the final determination result, and the erroneous determination of the state of the passenger on the child seat is prevented.

When the other passenger close to the child seat gets away from the child seat, both the first determination part 11 and the second determination part 12 can determine the passenger on the child seat to be "child", and the first determination result and the second determination result are the same as each other, and the third determination part 13 enters the normal state again. Thus, the third determination part 13 determines "child" of the first determination result to be the final determination result of the state of the passenger on the child seat, and the correct determination is maintained.

In this manner, even when the first passenger information acquisition device 21 is the sensor 21b and the second passenger information acquisition device 22 is the camera 22b, the passenger state determination device 10 can prevent the erroneous determination.

Embodiment 4

FIG. 14 is a drawing illustrating a configuration of a passenger state determination system according to an embodiment 4. The configuration in FIG. 14 is similar to that in FIG. 1 except that a log data recording part 14 is added to the passenger state determination device 10 and a vehicle position calculation device 24 and a storage device 25 are additionally connected to the passenger state determination device 10.

The vehicle position calculation device 24 calculates a position of the vehicle mounting the passenger state determination device 10 based on a positioning signal received from a global navigation satellite system (GNSS), for example. The vehicle position calculation device 24 may have a function of correcting the position of the vehicle using a technique of autonomous navigation or map matching, for example.

The log data recording part 14 of the passenger state determination device 10 creates log data associating the information of the final determination result of the state of the passenger by the third determination part 13 with the position of the vehicle (the position of the vehicle calculated by the vehicle position calculation device 24) at a time when the final determination is performed, and stores the log data in the storage device 25. At this time, the log data recording part 14 makes the log data include information, as the information of the final determination result, whether the final determination result is the first determination result or the second determination result or the final determination result maintains the first determination result before the change.

The log data stored in the storage device 25 can be used for investigating a cause of an accident occurring in the vehicle, and can contribute to improvement in safety of the traveling of the vehicle.

FIG. 14 illustrates the vehicle position calculation device 24 and the storage device 25 as devices different from the passenger state determination device 10, however, one or both of them may be built in the passenger state determination device 10.

The flow charts in FIG. 2 and FIG. 3 illustrate the example that the determination by the second determination part 12 (Steps S104 and S111) is performed only when the first determination result is changed (the determination is YES in Step S102) and it is determined that the first determination result is not appropriate (the determination is NO in Step S105), however, both the determination by the first determination part 11 and the determination by the second determination part 12 may be constantly performed, and in this case, the log data recording part 14 may make the log data include the information of both the first determination result and the second determination result.

Embodiment 5

Figure 15:
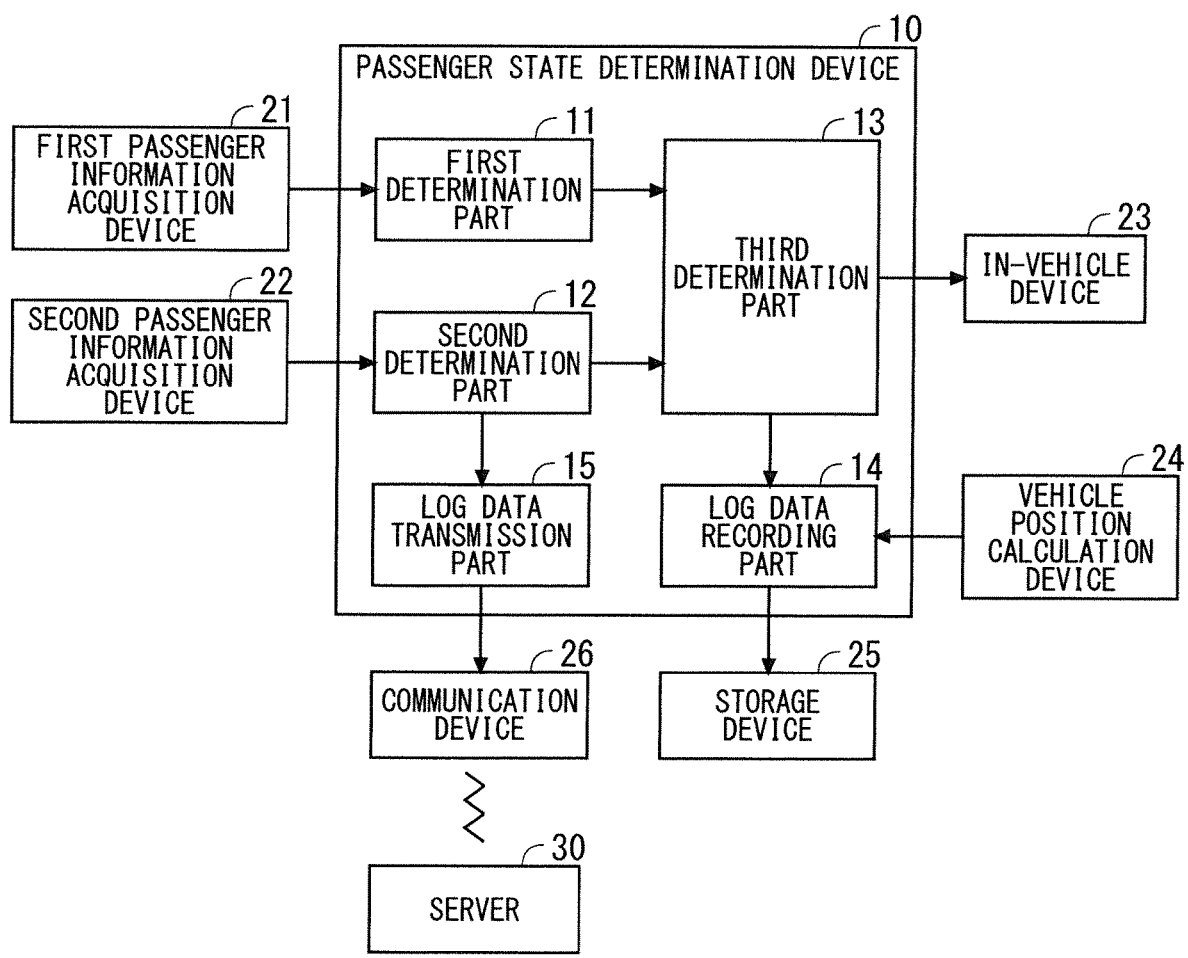
FIG. 15 A drawing illustrating a configuration of a passenger state determination system according to an embodiment 5.

FIG. 15 is a drawing illustrating a configuration of a passenger state determination system according to an embodiment 5. The configuration in FIG. 15 is similar to that in FIG. 14 except that a log data transmission part 15 is added to the passenger state determination device 10 and a communication device 26 which can communicate with a specific server 30 is additionally connected to the passenger state determination device 10.

The log data transmission part 15 transmits the log data created by the log data recording part 14 to the server 30 using the communication device 26. The log data transmission part 15 may transmit the log data to the server 30 constantly or at regular intervals. In other words, it is also applicable that the log data transmission part 15 transmits latest log data to the server 30 every time the log data recording part 14 creates the log data or collectively transmits log data stored in the storage device 25 to the server 30 in a certain period of time.

The server 30 is managed by a provider of the passenger state determination device 10, and the provider collects and analyzes the log data, thereby being able to use the log data for improvement of determination accuracy of the passenger state determination device 10, for example.

The communication device 26 may be a communication apparatus especially for the passenger state determination device 10, or may also be a general-purpose communication apparatus such as a mobile phone or a smartphone. When the communication device 26 is the communication apparatus especially for the passenger state determination device 10, the communication device 26 may be built in the passenger state determination device 10.

Each embodiment can be arbitrarily combined, or each embodiment can be appropriately varied or omitted.

The foregoing description is in all aspects illustrative, and it is therefore understood that numerous modification examples not exemplified can be devised.

EXPLANATION OF REFERENCE SIGNS

10 passenger state determination device, 11 first determination part, 12 second determination part, 13 third determination part, 14 log data recording part, 15 log data transmission part, 21 first passenger information acquisition device, 22 second passenger information acquisition device, 23 in-vehicle device, 24 vehicle position calculation device, 25 storage device, 26 communication device, 30 server, 21a, 22b camera, 21b, 22a sensor, 50 processing circuit, 51 processor, 52 memory, P1 passenger on driver seat, P2 passenger on rear seat, P3 passenger on front passenger seat.

The invention claimed is:

1. A passenger state determination device, comprising:
   a first determiner to determine a state of a passenger of a vehicle by a first method;
   a second determiner to determine a state of the passenger by a second method different from the first method; and
   a third determiner to finally determine a state of the passenger based on a first determination result as a determination result of the state of the passenger by the first determiner and a second determination result as a determination result of the state of the passenger by the second determiner, wherein
   the third determiner determines the first determination result to be a final determination result of the state of the passenger in a normal state, and
   when the first determination result is changed, the third determiner determines whether or not the first determination result after the change is appropriate based on the second determination result, and when the third determiner determines that the first determination result after the change is not appropriate, the third determiner determines the second determination result or the first determination result before the change to be a final determination result of the state of the passenger.

2. The passenger state determination device according to claim 1, wherein
   in a case where the first determination result is changed, the third determiner determines that the first determination result after the change is appropriate when the first determination result after the change and the second determination result coincide with each other, and determines that the first determination result after the change is not appropriate when the first determination result after the change and the second determination result do not coincide with each other.

3. The passenger state determination device according to claim 1, wherein
   the third determiner enters the normal state again and determines the first determination result to be a final determination result when the first determination result and the second determination result coincide with each other after the third determiner determines that the first determination result after the change is not appropriate.

4. The passenger state determination device according to claim 1, wherein
   the first determiner determines the state of the passenger based on an image of the passenger taken with a camera, and
   the second determiner determines the state of the passenger based on information of the passenger detected by a sensor.

5. The passenger state determination device according to claim 4, wherein
   the sensor is a radio-frequency sensor or an ultrasonic sensor disposed on an upper portion of a front seat of the vehicle.

6. The passenger state determination device according to claim 1, wherein
   the first determiner determines the state of the passenger based on information of the passenger detected by a sensor, and
   the second determiner determines the state of the passenger based on an image of the passenger taken with a camera.

7. The passenger state determination device according to claim 6, wherein
   the sensor is a radio-frequency sensor or an ultrasonic sensor disposed on an upper portion of a front seat of the vehicle.

8. The passenger state determination device according to claim 1, further comprising
   a log data recorder storing, in a storage device, log data including a final determination result by the third determiner and information whether the final determination result is a first determination result or a second determination result or the final determination result maintains a first determination result before change.

9. The passenger state determination device according to claim 8, further comprising
   a log data transmitter transmitting the log data to a specific server.

10. A passenger state determination method, comprising:
    determining a state of a passenger of a vehicle by a first method;
    determining a state of the passenger by a second method different from the first method; and
    finally determining a state of the passenger based on a first determination result as a determination result of the state of the passenger by the first method and a second determination result as a determination result of the state of the passenger by the second method, wherein
    the first determination result is to be a final determination result of the state of the passenger in a normal state, and
    when the first determination result is changed, it is determined whether or not the first determination result after the change is appropriate based on the second determination result, and when it is determined that the first determination result after the change is not appropriate, the second determination result or the first determination result before the change is to be a final determination result of the state of the passenger.

* * * * *